United States Patent [19]

Klemm

[11] Patent Number: Plant 6,441

[45] Date of Patent: Dec. 6, 1988

[54] CARNATION NAMED KLEGOFAS

[76] Inventor: Siegfried Klemm, Hanfacker 8, D 7000 Stuttgart 50, Fed. Rep. of Germany

[21] Appl. No.: 938,559

[22] Filed: Dec. 5, 1986

[51] Int. Cl.[4] ..... A01H 5/00
[52] U.S. Cl. ..... Plt./70
[58] Field of Search ..... Plt./70

*Primary Examiner*—Robert E. Bagwill

*Attorney, Agent, or Firm*—Charles W. Rummler

[57] ABSTRACT

A new carnation cultivar distinguished by its profuse production of light yellow flowers of medium size, each petal of which is bordered with a ruffled margin of a darker color, approaching pink with some striping of the pink color extending inwardly from the margin, the flowers being borne singly on strong, upright pedicels, which are carried on sturdy, upright peduncles, about 45 cm. long.

1 Drawing Sheet

BACKGROUND OF THE NEW PLANT

This new miniature carnation cultivar originated at Stuttgart, West Germany, as a sport of an unpatented carnation variety named "Klemstar", being grown in my greenhouses for the production of cut flowers, as well as for propagation and sale of plants to commercial growers for miniature carnation uses. This sport was discovered by me in my greenhouses at Stuttgart in 1981, and was selected for propagation because of its flowers having a light yellow coloration with the margins of its petals having a darker coloration, approaching pink. Asexual propagation of this new plant, by means of cuttings, has been carried out at Stuttgart, West Germany and in Italy and Israel, by me and under my direction through successive generations and the distinctive characteristics of this plant have been found to hold true for generation to generation and appear to be firmly fixed.

DESCRIPTION OF THE DRAWINGS

My new variety of miniature carnation plant is illustrated by the accompanying full color photographic drawing, which shows a group of flowering stems having buds in various stages of opening, newly opened flowers and blooms in further stages of maturity, the flower coloration being shown as merely true as it is reasonably possible to obtain by means of conventional photographic procedures.

DESCRIPTION OF THE NEW PLANT

The following is a detailed description of my new carnation variety, based upon observation of the plants grown under conventional greenhouse practices, with color designation being according to The Horticultural Colour Chart of Robert F. Wilson published by the British Colour Council in collaboration with the World Horticultural Society of London, England and The R.H.S. Colour Chart of The Royal Horticultural Society of London, England.

THE PLANT

Origin: Sport.
Parentage: Klemstar (unpatented).
Classification:
- *Botanic.*—*Dianthus caryophyllus.*
- *Commercial.*—Miniature.

Form: Bush.
Height: About 90 cm. to about 140 cm.
Growth: Vigorous and upright with moderate strength.
Branching: Normal.
Foliage:
- *Quantity.*—Moderate.
- *Leaf size.*—Moderate.
- *Leaf shape.*—Oblong.
- *Texture.*—Smooth.
- *Color.*—Upper side — Blue-green. Under side — Blue-green.

THE BUD

Size: Medium, about 15 mm. in diameter and about 38 mm. long.
Form: Generally cylindrical.
Opening rate: Moderate.
Color:
- *When sepals first divide.*—Yellow-green.
- *When petals begin to unfurl.*—Yellow-green.

Sepals:
- *Condition.*—Outstanding.
- *Color.*—Inside — Gray-green. Outside — Yellow-green.

Calyx:
- *Shape.*—Cylindrical.
- *Size.*—Moderate, about 16 mm. broad and about 18 mm. long.
- *Splitting.*—The calyx does not split.
- *Aspect.*—Smooth.
- *Peduncle.*—Rigid and erect.
- *Length.*—About 45 cm.
- *Color.*—Gray-green.

THE FLOWER

Blooming habit: Continuous and profuse.
Size of bloom: Medium.
- *Diameter.*—About 50 mm. to about 55 mm.
- *Depth.*—About 30 mm.

Borne: Singly on strong, upright pedicels.
Shape: Flat when the bloom opens. This shape does not change.
Petalage:
- *Number of petals.*—About 30.
- *Arrangement.*—Generally imbricated.
- *Shape.*—Fan-shaped with serrated margins.

*Color.*—Outer petal and inside petals — R.H.S. 2C-3D with margins of oriental red and fine oriental red stripes occasionally extending lengthwise from tips of petal ruffles — HCC 819-819/1.

*Texture.*—Soft.

*Appearance.*—Shiny.

Peduncle: Sturdy and upright.

*Length.*—About 45 cm.

*Color.*—Gray-green.

Persistence: The petals hang on and dry and the bloom stays upright.

Fragrance: None.

Lasting quality:

*On plant.*—About 14 days.

*As a cut flower.*—About 12 days.

REPRODUCTIVE ORGANS

Stamens: Anthers and pollen are rarely present.

*Filaments.*—Color — white.

*Pollen.*—Color — white.

Pistils: Not more than three.

*Styles.*—Length — about 36 mm.

*Stigmas.*—Color — cream white.

Fruit: Fertile.

*Color.*—Green/Brown at maturity.

This new miniature carnation variety somewhat resembles the variety "Klemstar". However, it has a new and different flower color.

I claim:

1. A new and distinct carnation variety, substantially as herein shown and described, characterized by its continuous production of light yellow flowers of medium size having petals which have a ruffled margin of a darker color, approximating orient red.

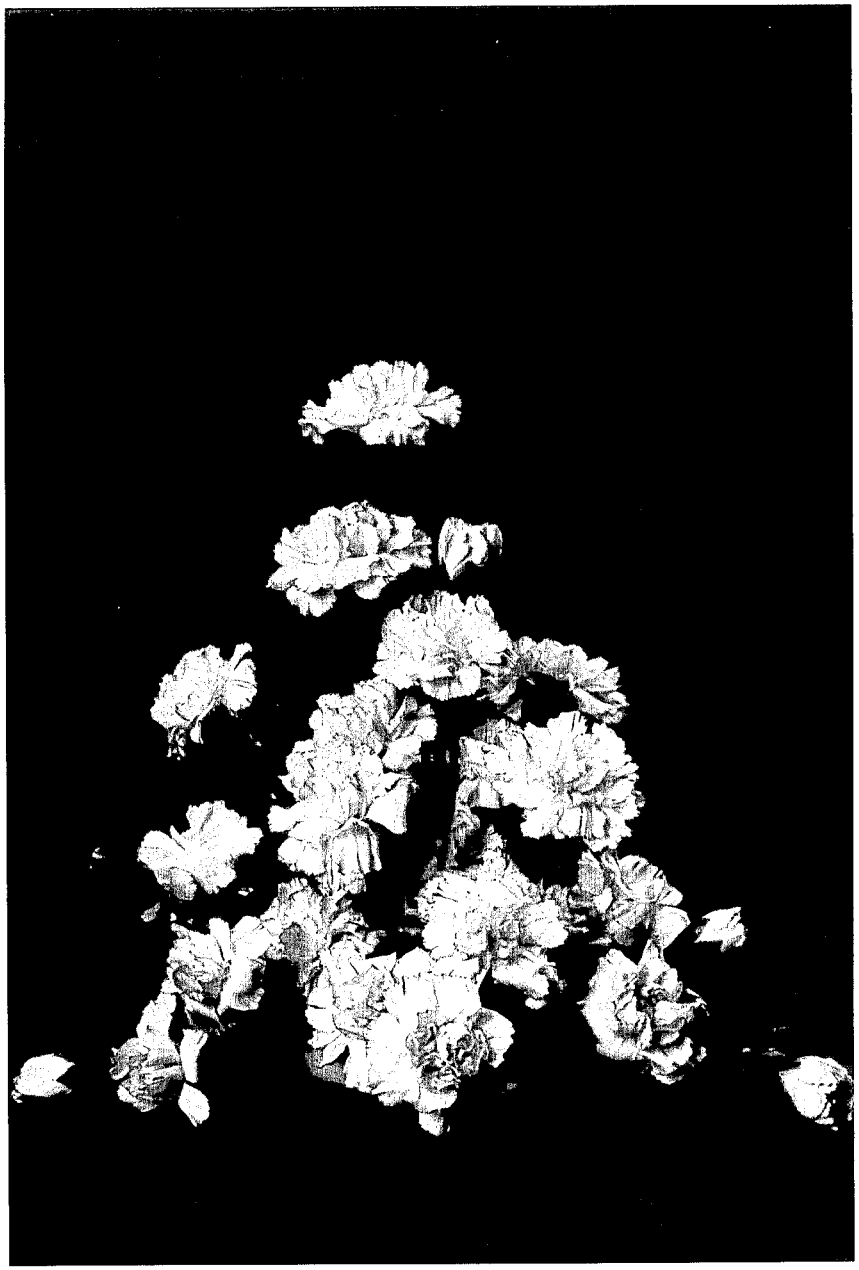

* * * * *